United States Patent [19]

Slomski

[11] 4,035,066

[45] July 12, 1977

[54] APPARATUS FOR TESTING STEREOSCOPIC VISION

[76] Inventor: Waclaw Kazimierz Slomski, 426 Wilkinson St., Syracuse, N.Y. 13204

[21] Appl. No.: 557,662

[22] Filed: Mar. 19, 1975

[51] Int. Cl.$^2$ .......................................... A61B 3/08
[52] U.S. Cl. ...................................... 351/3; 351/33
[58] Field of Search ................................. 351/3, 33

[56] References Cited

U.S. PATENT DOCUMENTS

| 1,954,399 | 4/1934 | Ames, Jr. | 351/3 |
| 2,033,634 | 3/1936 | Higley | 351/3 |

FOREIGN PATENT DOCUMENTS

| 982,874 | 2/1965 | United Kingdom | 351/33 |

Primary Examiner—Paul A. Sacher
Attorney, Agent, or Firm—Mason, Mason & Albright

[57] ABSTRACT

Equipment to test psychologically drivers of all kinds of motor vehicles, and in particular, to test stereoscopic vision. The testing of stereoscopic vision consists in checking up the competence of spatial perception, necessary for distance evaluation.

The equipment consists of two main parts: a measuring and recording device, and a control desk of the tested person.

The test consists of aligning two measuring rods with the third one, which is in the middle, and is immobilized. The tested person looks through a slot in the wall of the control desk, and operates an aligning mechanism. The results of the test are automatically recorded on the recording plate of the equipment.

3 Claims, 4 Drawing Figures

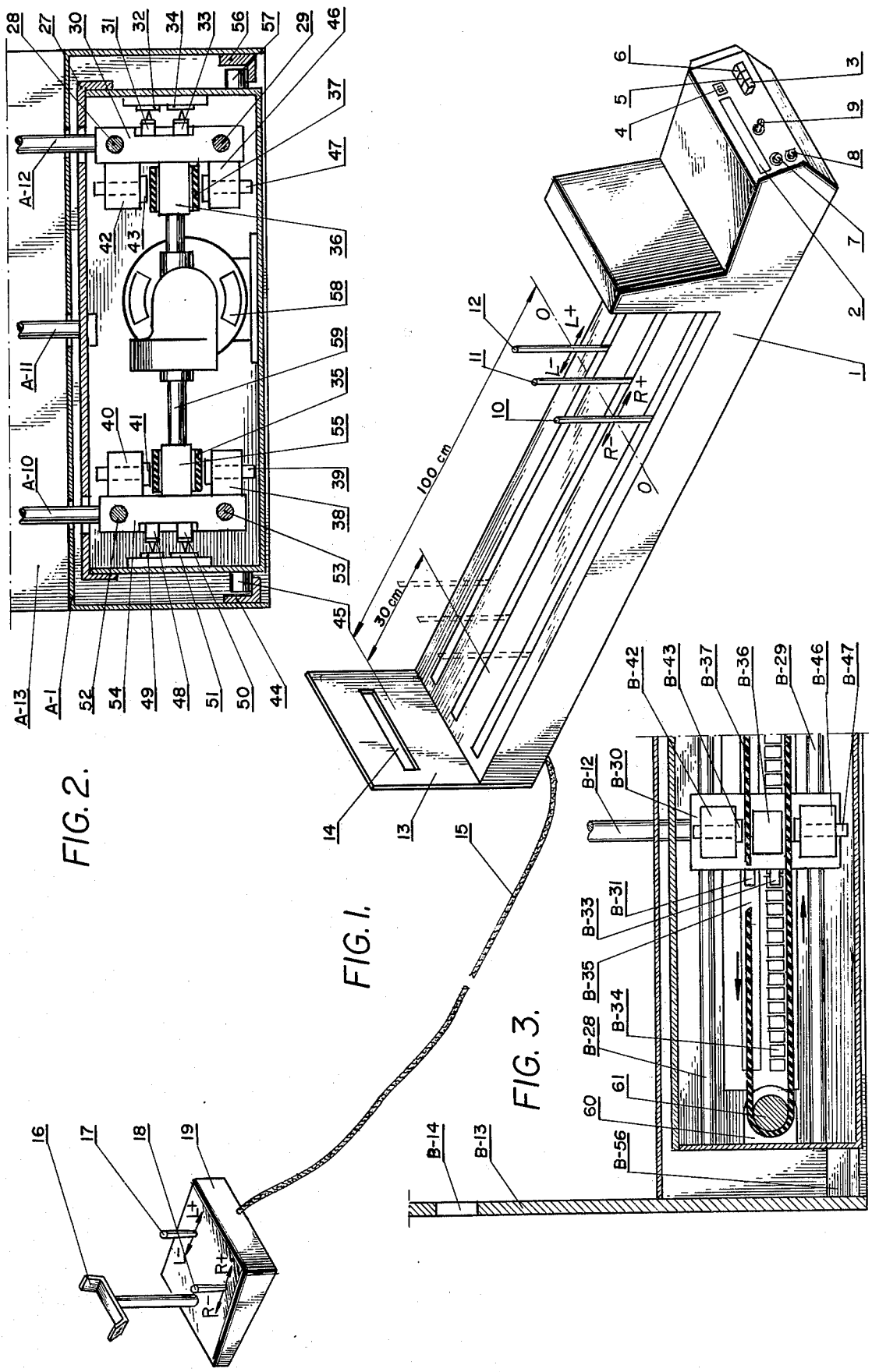

APPARATUS FOR TESTING STEREOSCOPIC VISION

BACKGROUND OF THE INVENTION

The enormous development of street and highway traffic results in a steadily growing number of traffic accidents. These accidents bring about great material losses and, more importantly, are incommensurable in relation to human losses: loss of life, or permanent invalidism. The safety of traffic on the highways and streets depends to a considerable degree an the fact that the driver successfully reacts in a definite traffic situation in a proper way and sufficiently fast. The psychology of street and highway traffic tries to explain these problems. The subject of its investigation is a detailed analysis of the driver's work in order to establish psycho-physiological functions indispensable for its safe execution. The driver's work has a specific character. In addition to some acquired information a training and possession of driving competence, the driver is also required to possess a particular psycho-physiological competence, considering the dynamics of the driven vehicle, and the connected with it human life and health hazards.

Among the great number of drivers, traveling on the streets and highways, there are some who often do not realize that they have certain psycho-physiological deficiences. This is why a necessity arises for controlling psycho-physiological characteristics of drivers before their licensing, and during their execution of work, as concerns changes, or disappearance of psycho-physiological competence.

The proper evaluation of psycho-physiological characteristics of a driver can be made only by using certain equipment, specialized and adapted for this aim. One which serve such aims is my present invention. With the help of the instant invention one can test stereoscopic vision. This test consists on checking up the competence of spatial perception, necessary for evaluating the distance. This feature is of great importance from the point of view of requirements of driver's work.

OBJECTS OF THE INVENTION

The invention comprises the feature of construction, combination of elements, and arrangements of parts, which will be exemplified in the construction hereinafter set forth, and the scope of the invention will be indicated in the Claims.

The invention has will have a wide application in testing people. It is primarily intended for psychological testing drivers of all kinds of motor vehicles. One can also test other people, who work in certain specific conditions, or for qualifying people for certain professions, where the competence of spatial perception, necessary for evaluating distance, is required.

The invention is one type of equipment which together with other testing apparatus form a set, serving a method of psychological test for drivers of all kinds of motor vehicles. These tests aim at the reduction of the number of road and street traffic accidents, which will contribute to the improvement of traffic safety on the roads.

For a fuller understanding of the nature and objects of the invention, reference should be had to the following detailed description, taken in connection with the accompanying drawings, in which:

BRIEF DESCRIPTION OF THE DRAWINGS

FIG. 1 is a perspective view of the invention consisting of the measuring-and-recording device and of the control desk.

FIG. 2 presents a cross-section, made across the system of the measuring-and-control mechanism.

FIG. 3 presents the longitudinal section, made across the measuring-and-driving mechanism.

DESCRIPTION OF THE PREFERRED EMBODIMENTS

Figure 4:
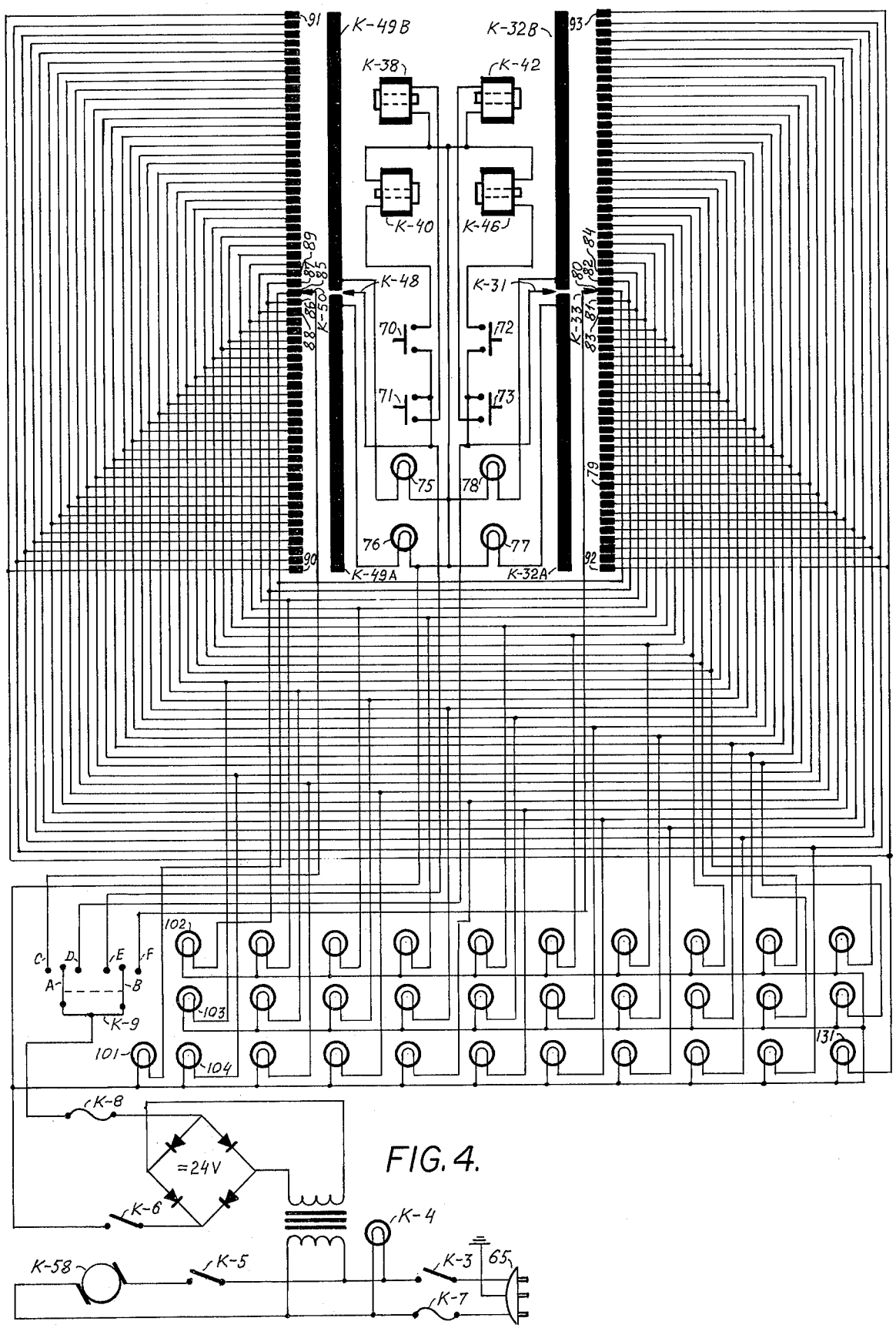
FIG. 4 is an electric circuit diagram of the equipment.

The invention comprises two basic parts, i.e. (1) the measuring-and-recording apparatus, which is conn-nected by a multiwire cable with (2) the control desk.

FIG. 1 shows in perspective the measuring-and-recording device. On the distribution board of the device are located the following elements: recording scale 2, which registers results of tests; switch 3 of the supply 115V network; control lamp 4, signaling the connection of the device to the 115V network; switch 5 for the connection of the driving mechanism motor; switch 6 for the connection of the supply system of the device; fuse 7 protecting the 115V network; fuse 8 protecting the supply system of the device. Under the casing 1 of the device, the driving system of the mechanism is located, where the three of its measuring rods can be seen: The right rod 10, the middle rod 11, and the left rod 12. All the driving mechanism has the possibility of shifting forward and backwards, along the casing 1. In this way there exists a possiblity of double testing, i.e., when the 0—0 line of the middle measuring rod 11 is at a distance of 30 cm, or alternatively 100 cm from the back wall 13 of the device. In the back wall 13 a horizontal longitudinal opening 14 is made. The measuring-and-recording device is connected with the control desk by a multiwire cable 15. A support 16 is fixed to the upper plate of the casing 19 of the control desk, and also two double push-buttons: The right-side double push-button, the lever 18 of which is visible, and the left-side double push-button, the lever 17 of which is visible. These push-buttons short-circuit the current-circuit during the moving of the corresponding levers forward or backwards, i.e., in the direction R+, R—, and L+, L—.

FIG. 2 presents a cross-section of the driving mechanism system. Under the casing A-1 of the device is located the cover 27 of the driving mechanism. All the elements of the driving mechanism are fixed under this cover. The driving mechanism is positioned with rollers 45 and 57 on support-elbows 44 and 56, which secures the longitudinal shift of the mechanism. On the background of the back wall A-13 are seen the measuring rods: the right measuring rod A-10, the middle measuring rod A-11, and the left measuring rod A-12. The middle measuring rod A-11 is permanently fixed to the mechanism cover 27, whereas the side measuring rods can be shifted forwards and backwards, relative to the middle rod A-11, along the casing 1 of the measuring-and-recording device. The right measuring rod A-10 moves with its frame 54 along its guide-rails 52 and 53; the left measuring rod A-12 moves with its frame 30 along its guide-rails 28 and 29. The side measuring rods are shifted with the help of flat driving belts 35 and 37, which are driven by the electrical motor 58. Electromagnets 38 and 40are fastened to the frame 54 of the right measuring rod, and electro-magnets 42 and 46 are fastened to the frame 30 of the left measuring rod. The respective electro-magnets serve to switch in and switch off the shift of respective measuring rods. The cores of the electro-magnets 39 and 41, and 43 and 47, serve for tightening the driving belts 35 and 37 to the buffers 36 and 55. The brush 48 finds itself on the area 49 of the direction setting of the right measuring rod A-10, and the brush 50 on the contact plates 51 of the place setting of the measuring rod A-10. The brush 31 finds itself on the area 32 of the direction setting of the measuring rod A-12, and the brush 33 on the contact plates 34 of the place setting of the measuring rod A-12.

FIG. 3 presents the longitudinal profile of the driving mechanism system, where one can see only the left side of the driving-and-measuring system. The measuring rod B-12 is secured with the frame B-30. The frame B-30 is settled on the upper guide-rail B-28 and the lower guide-rail B-29, and can move in parallel, horizontally forward, in the direction L+, and backwards, in the directin L—, FIG. 1. The driving belt B-37 is fastened on one side of the roller 61 of the support 60 and on the other side on the driving axis 59. FIG. 2 of the motor 58, FIG. 2. The driving belt B-37 turns only in one direction with constant speed, according to the arrows. Electro-magnets B-42 and B-46 are fastened to the frame B-30. The electro-magnets B-42, after the operation, presses with the core B-43 the driving belt B-37 to the buffer B-36, which causes the shift of the measuring rod in the direction of L—. After the switching off the electro-magnet B-42, the core B-43 releases the pressure of the driving belt, and the measuring rod B-12 is stopped. The shift of the measuring rod in the direction of L+ causes the operation of the electro-magnet B-46. Then the core B-47 presses the driving belt B-37 to the buffer B-36. In the same way, the measuring rod A-10, FIG. 2, is being shifted.

METHOD OF CONDUCTION TESTS

The person tested sits in front of the control desk resting his chin on the support 16, FIG. 1. The measuring-and-recording device is located in front of the tested person in such a way, that the distance of the back wall 13, FIG. 1 from the tested person's eyes is 3 meters. The tested person sitting at the control desk can see across the longitudinal opening 14, FIG. 1, only the central fragments of the measuring rods. The middle measuring rod 11, FIG. 1, is immobile, while the right measuring rod 10, and the left measuring rod 12 can be moved forward or backwards of the line 0—0, FIG. 1, of the rod 11 in parallel to each other.

The task of the tested person consists in looking through the opening 14, FIG. 1, to align during a prescribed period of time, first the right measuring rod 10, and then the left measuring rod 12 with the line 0—0 of the middle measuring rod 11. This aligning is done by remote control, using for this purpose the levers of the push-buttons 17 and 18. The pressing of the right lever 18 in the direction of R+ causes the shift of the right measuring rod 10 forward in the direction of R+. The pressing of the lever 18 backwards, in the direction of R—, causes the shift of the right measuring rod 10 backwards, in the direction of R—. Every deviation forward or backward relative to the line 0—0 of the middle measuring rod 11 is displayed on the scale 2, FIG. 1, which registers the results of tests. One can read from the recording scale 2 the direction of placement of the given measuring rods, and their exact location. The direction of the arrangement determines where the givenmeasuring rod is placed. For example, the indication R+ on the recording scale indicates, that the right measuring rod 10 is advanced forward of the line 0—0 of the middle measuring rod 11. The indication L— on the recording scale determines that the left measuring rod 12 is shifted-backwards of the line 0—0 of the middle measuring rod 11. The place of arrangement determines how far the given measuring rod is placed from the line 0—0 of the middle measuring rod 11. For example, the indication on the recording scale R— and digit 25 shows that the right measuring rod 10 is moved back from the line 0—0 of the middle measuring rod 11 by 25 mm.

The resulting of testing is the difference between the location of the measuring rods 10 and 12 in relation to line 0—0 of the middle measuring rod 11, measured in mm. The difference of location is measured separately for each measuring rod.

The testing is carried on twice. The first time, the middle rod 11 is located at a distance of 100 cm from the back wall 13, and the second time, when the middle rod 11 is located at a distance of 30cm from the back wall 13, FIG. 1. FIG. 4 presents the electric diagram of the equipment. The equipment is supplied from the 115V/60Hz network.

The equipment elements are supplied by direct current at 24V. After connecting the plug 65 to the socket of the electric network and pushing-in the pushbutton switch K-3, the signal lamp K-4 is lighted and, simultaneously, the 24V rectifier is connected. Before starting the tests, the change-over switch K-9 is switched-on in the short-circuiting of A-C and B-E conductors position. Then there exists only the possibiltiy of controlling the right measuring rod. After the switching-on the K-5 switch, the motor K-58 of the driving mechanism is set in motion. The fuse K-7 serves to protect the 115-V supply network, and the fuse K-8 serves to protect the 24-V supply network. With the switching-on the switch K-6, the equipment is ready for testing. The tested person can set up the right measuring rod. If the K-50 brush is placed on the contact plate 91 of the location of the right measuring rod, then the K-48 brush will be placed on the contact field K-49B of the direction of arrangement of the measuring rod. Then current will flow through the change-over switch K-9, position B-E, to the brush K-48, and through the contact field K-49B to the electric bulb 75. The bulb 75 will light from below the sign R— on the recording scale, which means that the right measuring rod 10, FIG. 1, finds itself towards the back from the line 0—0 of the middle measuring rod 11, FIG. 1, in the direction of the tested person. On the other hand, the arrangement of the K-50 brush on the contact plate 91 will cause the switching on of the electric bulb 131, which indicates that the right measuring rod is placed towards the back, at a distance of 150 mm from the line 0—0, FIG. 1, of the middle measuring rod 11. Therefore, on the recording scale illumination occurs below the sign R— and the digit 150. In order to move the right measuring rod towards the line 0—0, FIG. 1, of the middle measuring rod 11, one has to press the lever 18, FIG. 1, in the direction R°. Then the push-button 71 will be switched-on, which will set in motion the electro-magnet K-38. The operation of the electromagnet K-38 causes the shift of the frame 54, FIG. 2, to which are fastened the right measuring rod 10 and the respective brushes. The brush K-50, gliding on contact plates, establishes the place of arrangement of the right measuring rod, and the brush K-48, gliding on the contact field, establishes the direction of the arrangement of the right measuring rod. The location of the brush K-50 on the contact plate 85 fixes the location of the right measuring rod on the line 0—0, FIG. 1, of the middle measuring rod 11. This location can be read on the recording scale, where the electric bulb 101 will light from below the digit 0. With the indication of 0 on the recording scale, the brush K-48 is arranged on the insulating field, and during this time, none of the electric bulbs 75, 76, 77 and 78 is lighted. These bulbs serve for lighting from below on the recording scale the corresponding signs of the direction of the location of the given measuring rod. The bulb 75 lights from below the sign R—, which indicates that the right measuring rod 10, FIG. 1, is to the rear of the line 0—0, FIG. 1, of the middle measuring rod 11, FIG. 1, in the direction towards the tested person. The electric bulb 76 lights up from below the sign R+, which indicates that the right measuring rod is ahead from the line 0—0, FIG. 1, of the middle measuring rod 11, FIG. 1, in the direction from the tested person. The electric bulb 77 lights up from below the sign L+ on the recording scale 2, FIG. 1, which indicates that the left measuring rod 12, FIG. 1, is placed ahead of the line 0—0, FIG. 1, of the middle measuring rod 11, FIG. 1, in the direction from the tested person. The electric bulb 78 lights up from below the sign L— on the recording scale 2, FIG. 1, which indicates that the left measuring rod 12, FIG. 1, is placed to the rear from the line 0—0, FIG. 1, of the middle measuring rod 11, FIG. 1, in the direction towards the tested person.

The switching on of the push-button 71 causes the operation of the electro-magnet K-38, and the shift of the right measuring rod 10, FIG. 1, together with the brushes K-48 and K-50 towards R+, FIG. 1.

The switching on of the push-button 70 causes the operation of the electro-magnet K-40, and the shift of the right measuring rod 10, FIG. 1, together with the brushes K-48 and K-50 in the direction of R—, FIG. 1.

The switching on of the push-button 72 causes the operation of the electro-magnet K-46, and the shift of the left measuring rod 12, FIG. 1, together with the brushes K-31 and K-33, in the direction of L+, FIG. 1.

The switching on of the push-button 73 causes the operation of the electro-magnet K-42, and the shift of the left measuring rod 12, FIG. 1, together with the brushes K-31 and K-33 in the direction of L—, FIG. 1.

The several contact plates of the right side are interconnected in pairs symmetrically in relation to the zero contact plate 85. For example, contact plate 86 is connected with the contact plate 87, and contact plate 88 is connected with contact plate 89, etc., up to the last contact plates, where contact plate 90 is connected with the contact plate 91. The several pairs of contact plates of the right side are correspondingly connected with the pairs of contact plates of the left side. For example, the contact plates of the right side 85 and 86 are connected with the pair of contact plates of the left side 80 and 81. In the corresponding way all pairs of the measuring plates of the right side are connected with the corresponding measuring plates of the left side. Such connection of measuring plates permits to use the same system recording the results of tests for the right side as well as for the left side.

After the setting up of the right measuring rod 10 by the tested person, the change-over switch K-9 is set in the position A-D and B-F. At this moment the right side of the driving mechanism is switched off, and the left side of the driving mechanism is switched on. The appropriate electro-magnets K-42 and K-46 are set in operation by push-buttons 72 and 73, shifting in this way the left measuring rod 12, FIG. 1, ahead to L+, in the direction from the tested person, or to the rear, L—, in the direction towards the tested person. The brush K-33, arranged on the appropriate contact plate, establishes the location of the left measuring rod 12, FIG. 1. On the other hand, the brush K-31, arranged on the contact field K-32A, establishes the direction of the position of the left measuring rod 12, FIG. 1, as L+, that means ahead of the line 0—0, FIG. 1, in the direction from the tested person. The brush K-31, arranged on the contact field K-32B, establishes the direction of the position of the left measuring rod 12, FIG. 1, as L—, i.e., to the rear of the line 0—0, FIG. 1, in the direction towards the tested person.

The place of arrangement of the left measuring rod can be read on the recording scale, where the appropriate electric bulb will light from below the corresponding digit. For example, when the brush K-33 will be set on the contact plate 79, then the current will flow and will switch on the electric bulb 104, which will light up the digit 105 on the recording scale, which means that the left measuring rod 12, FIG. 1, is located at the distance of 105mm from the line 0—0, FIG. 1, of the middle measuring rod 11, FIG. 1. On the other hand, the brush K-31 will be set on the contact field K-32A, which determines the direction of the location of the left measuring rod as L+, i.e., ahead of the line 0—0, FIG. 1, of the middle measuring rod, in the direction from the tested person. When the brush K-31 will be set on the contact field K-32A, then the current will flow and will light up the electric bulb 77, which will light up from below the sign L+ on the recording scale.

By analyzing the results, obtained during the tests, one will be able to evaluate the tested person as to the degree of the given psycho-physiological feature possessed, and thereby to foresee good or bad results of performing the task for which this person was tested.

The above described equipment has been built as a model. All its electric and mechanical systems operate accurately, and meet perfectly the requirements. The equipment can unreservedly be used for psychological tests.

Having described my invention, what I claim as new, and desire to secure by Letters Patent, is:

1. Apparatus for testing stereoscopic vision which comprises:
   a casing having at least two longitudinal parallel side-by-side paths,
   a mechanism mounted in said casing to be movable parallel to said paths and to be selectively positioned at various locations therein,
   a first measuring means affixed to said mechanism which is located in one of said paths,
   a second measuring means movably mounted in said mechanism which is in the other of said paths, driving means mounted in said mechanism for moving said second measuring means in either direction relative thereto and connective means for selectively connecting said second measuring means to said driving means,
   a control desk provided with means for directing movement of said measuring means in either direction along said other path by actuating said connective means, said control desk being selectively fixed relative to said casing whereby a person being tested who is located at said control desk simultaneously views both said measuring means and controls the movement of said second measuring means to align same with said first measuring means by selectively connecting said second measuring means to said driving means.

2. Apparatus for testing stereoscopic vision in accordance with claim 1 wherein said driving means comprises a continuously moving endless member.

3. Apparatus for testing stereoscopic vision in accordance with claim 2 wherein said mechanism includes a plurality of electrically conductively segments, electrical control means interconnecting said second measuring means and at least one of said segments the position of which is dependent on its distance relative to said first measuring means, circuit means between said interconnection and a registration means provided to register the relative distance longitudinally along said paths between said first and said second measuring means.

* * * * *